(12) United States Patent  (10) Patent No.: US 8,941,824 B2
Nakanishi et al.  (45) Date of Patent: Jan. 27, 2015

(54) SEMICONDUCTOR INSPECTION METHOD AND SEMICONDUCTOR INSPECTION APPARATUS

(75) Inventors: Hidetoshi Nakanishi, Kyoto (JP); Masayoshi Tonouchi, Suita (JP)

(73) Assignees: Dainippon Screen Mfg. Co., Ltd., Kyoto (JP); Osaka University, Osaka (JP)

( * ) Notice: Subject to any disclaimer, the term of this patent is extended or adjusted under 35 U.S.C. 154(b) by 178 days.

(21) Appl. No.: 13/621,038

(22) Filed: Sep. 15, 2012

(65) Prior Publication Data
US 2013/0083319 A1 Apr. 4, 2013

(30) Foreign Application Priority Data

Sep. 29, 2011 (JP) .................................. 2011-214229

(51) Int. Cl.
G01N 21/00 (2006.01)
G01N 21/95 (2006.01)
G01N 21/17 (2006.01)
G01R 31/311 (2006.01)
G01N 21/956 (2006.01)

(52) U.S. Cl.
CPC ........ G01N 21/9501 (2013.01); G01N 21/1717 (2013.01); G01R 31/311 (2013.01); G01N 21/956 (2013.01)
USPC .................................... 356/237.5; 250/341.4

(58) Field of Classification Search
None
See application file for complete search history.

(56) References Cited

U.S. PATENT DOCUMENTS

| 4,454,472 A | 6/1984 | Moore |
| 7,173,447 B2* | 2/2007 | Yamashita et al. ....... 324/754.23 |
| 2006/0006886 A1 | 1/2006 | Yamashita et al. |
| 2011/0216312 A1 | 9/2011 | Matsumoto et al. |

FOREIGN PATENT DOCUMENTS

| EP | 1441233 A1 | 7/2004 |
| JP | 05226431 A | 9/1993 |
| JP | 2006-024774 A | 1/2006 |
| WO | WO-99/13318 A1 | 3/1999 |

OTHER PUBLICATIONS

European Search Report issued in European Patent Application No. 12184081.3 dated Jan. 30, 2013.

* cited by examiner

*Primary Examiner* — Tarifur Chowdhury
*Assistant Examiner* — Amanda Merlino
(74) *Attorney, Agent, or Firm* — McDermott Will & Emery LLP

(57) ABSTRACT

A semiconductor inspection apparatus (100) is an apparatus for inspecting a semiconductor device. The semiconductor inspection apparatus (100) includes a pulsed laser light source (14) for emitting pulsed laser light (2) toward a substrate (1) with a semiconductor device formed thereon, an electromagnetic wave pulse application part (18) for applying a reverses-biasing electromagnetic wave pulse (4) for applying a reverse bias to an application position (10) which receives the pulsed laser light (2), and a detection part (17) for detecting an electromagnetic wave pulse (3) emitted from the application position (10) in response to the application of the pulsed laser light (2).

6 Claims, 8 Drawing Sheets

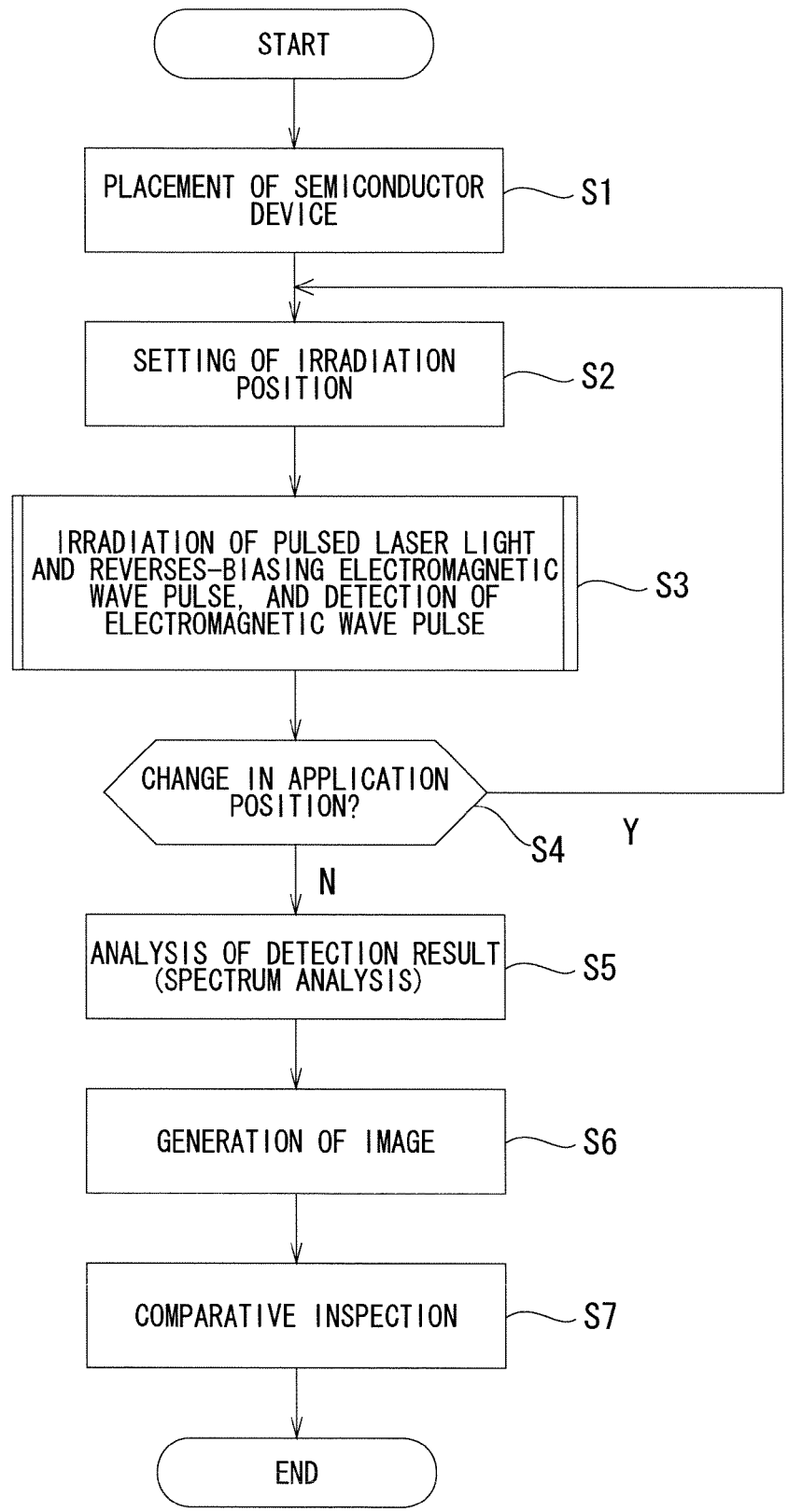
F I G. 5

F I G . 7
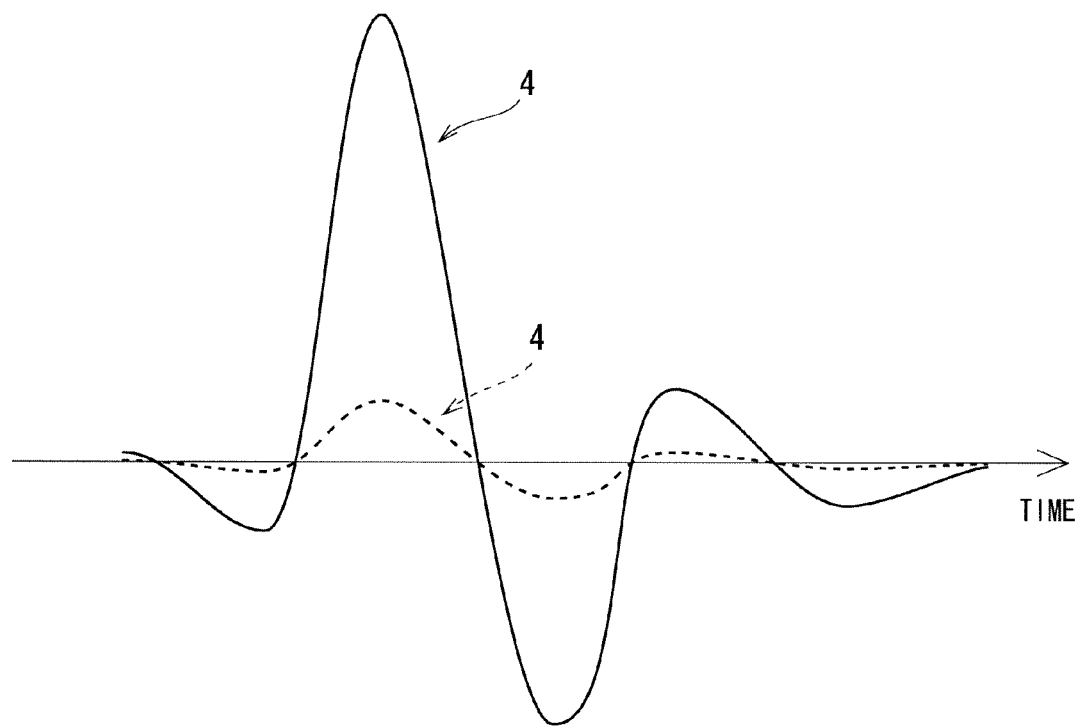

SEMICONDUCTOR INSPECTION METHOD AND SEMICONDUCTOR INSPECTION APPARATUS

BACKGROUND OF THE INVENTION

1. Field of the Invention

The present invention relates to a technique which uses pulsed laser light to inspect a semiconductor device and, more particularly, to a technique for increasing the electric field strength of an electromagnetic wave pulse generated from a semiconductor device in response to the irradiation of pulsed laser light to the semiconductor device.

2. Description of the Background Art

There have been proposed methods of detecting various defects, such as a defective location at a pn junction, and a break, a short circuit and a high-resistance location in an interconnect line, for the purpose of conducting a failure analysis and a fault analysis on semiconductor devices.

A known example of the technique of inspecting a semiconductor device is a technique which detects an OBIC (optical beam induced current) phenomenon. For this inspection in which a reverse-bias voltage is applied to a semiconductor device, it is necessary to perform a bonding process on the semiconductor device, thereby electrically connecting the semiconductor device to an external voltage application apparatus. In the course of the steps of manufacturing a semiconductor device, it is difficult to connect the semiconductor device to the external voltage application apparatus. A technique is hence proposed which inspects a semiconductor device in a non-contacting manner, as disclosed in Japanese Patent Application Laid-Open No. 2006-24774, for example.

Specifically, the inspection method disclosed in Japanese Patent Application Laid-Open No. 2006-24774 is a method which applies pulsed laser light to a semiconductor device to detect various defective locations. Upon receiving pulsed laser light, part of a semiconductor device where an electric field is present such as a pn junction generates an electromagnetic wave pulse. Based on the detection of the generated electromagnetic wave pulse, the detection of defective locations in the semiconductor device is performed. Such an inspection method is capable of inspecting a semiconductor device in a non-contacting method. This allows such an inspection method to handle a semiconductor device being subjected to the manufacturing steps as an object to be inspected.

In the inspection method disclosed in Japanese Patent Application Laid-Open No. 2006-24774, the inspection is conducted without the reverse-bias voltage applied to the semiconductor device for the purpose of accomplishing the inspection in a non-contacting manner. However, the electric field present inside the semiconductor device is relatively weak. The electric field strength of the generated electromagnetic wave pulse is accordingly extremely low. It is hence difficult to detect the extremely low electric field strength in some cases. For this reason, it has been necessary to decrease noise components by optimizing the apparatus configuration or the measurement conditions of an inspection apparatus, thereby improving the sensitivity of measurement of the electromagnetic wave pulse. Thus, preparatory operations require a large amount of time and complexity. A technique which improves the sensitivity of detection of an electromagnetic wave pulse in a non-contacting manner is therefore desired.

SUMMARY OF THE INVENTION

The present invention is intended for a semiconductor inspection apparatus for inspecting a semiconductor device.

According to a first aspect of the present invention, the semiconductor inspection apparatus comprises: a first irradiation part for irradiating pulsed laser light to a semiconductor device; a second irradiation part for irradiating a reverse-biasing electromagnetic wave pulse for applying a reverse bias to an irradiation position which receives the pulsed laser light; and a detection part for detecting an electromagnetic wave pulse emitted from the irradiation position in response to the irradiation of the pulsed laser light.

The semiconductor inspection apparatus according to the first aspect is capable of applying the reverse bias in a non-contacting method to increase the intensity of the emitted electromagnetic wave pulse. Also, the semiconductor inspection apparatus is capable of irradiating the reverse-biasing electromagnetic wave pulse to any location to thereby apply the reverse bias to any location.

Preferably, in the semiconductor inspection apparatus according to a second aspect of the present invention, the second irradiation part uses a light source identical with a light source for generating the pulsed laser light to generate the reverse-biasing electromagnetic wave pulse.

The semiconductor inspection apparatus according to the second aspect may use the light source of the pulsed laser light to reduce the number of components of the apparatus. This also facilitates the irradiation of the pulsed laser light and the reverse-biasing electromagnetic wave pulse in synchronism with each other to the irradiation position.

Preferably, in the semiconductor inspection apparatus according to a third aspect of the present invention, the second irradiation part applies the reverse-biasing electromagnetic wave pulse so that the direction of an electric field applied to the irradiation position by the irradiation of the reverse-biasing electromagnetic wave pulse is from an n-type semiconductor to a p-type semiconductor.

The semiconductor inspection apparatus according to the third aspect is capable of applying the electric field directed from the n-type semiconductor to the p-type semiconductor to thereby apply the reverse bias. This appropriately increases the electric field strength of the electromagnetic wave pulse.

Preferably, the semiconductor inspection apparatus according to a fourth aspect of the present invention further comprises a structure specifying part for specifying the structure of a semiconductor in the irradiation position.

The semiconductor inspection apparatus according to the fourth aspect specifies the structure of the semiconductor in the irradiation position to apply the reverse bias, thereby appropriately determining the direction of the electric field to be applied.

Preferably, the semiconductor inspection apparatus according to a fifth aspect of the present invention further comprises a scanning mechanism for moving the irradiation position of the pulsed laser light to thereby scan the semiconductor device two-dimensionally.

The semiconductor inspection apparatus according to the fifth aspect is capable of conducting the inspection which applies the pulsed laser light over a predetermined range of the semiconductor device.

The present invention is also intended for a method of inspecting a semiconductor device.

According to a sixth aspect of the present invention, the method comprises the steps of: (a) irradiating pulsed laser light having a desired wavelength to a semiconductor device; (b) irradiating a reverse-biasing electromagnetic wave pulse to apply a reverse bias to an irradiation position which receives the pulsed laser light in the step (a); and (c) detecting an electromagnetic wave pulse emitted from the irradiation position in response to the irradiation of the pulsed laser light.

It is therefore an object of the present invention to provide a technique which improves the intensity of an electromagnetic wave pulse generated from a semiconductor device in response to the irradiation of pulsed laser light to the semiconductor device in a non-contacting manner.

These and other objects, features, aspects and advantages of the present invention will become more apparent from the following detailed description of the present invention when taken in conjunction with the accompanying drawings.

BRIEF DESCRIPTION OF THE DRAWINGS

FIG. 5 is a flow diagram for an inspection of a semiconductor device in the semiconductor inspection apparatus;

FIG. 7 is a graph showing waveforms of an electromagnetic wave pulse generated when a reverse bias is applied (a solid curve) and an electromagnetic wave pulse generated when no reverse bias is applied (a broken curve) over time.

DESCRIPTION OF THE PREFERRED EMBODIMENTS

A preferred embodiment according to the present invention will now be described in detail with reference to the accompanying drawings. Components described in the preferred embodiment are merely illustrative, and are not intended to limit the technical scope of the present invention.

<1. First Preferred Embodiment>

Figure 1:
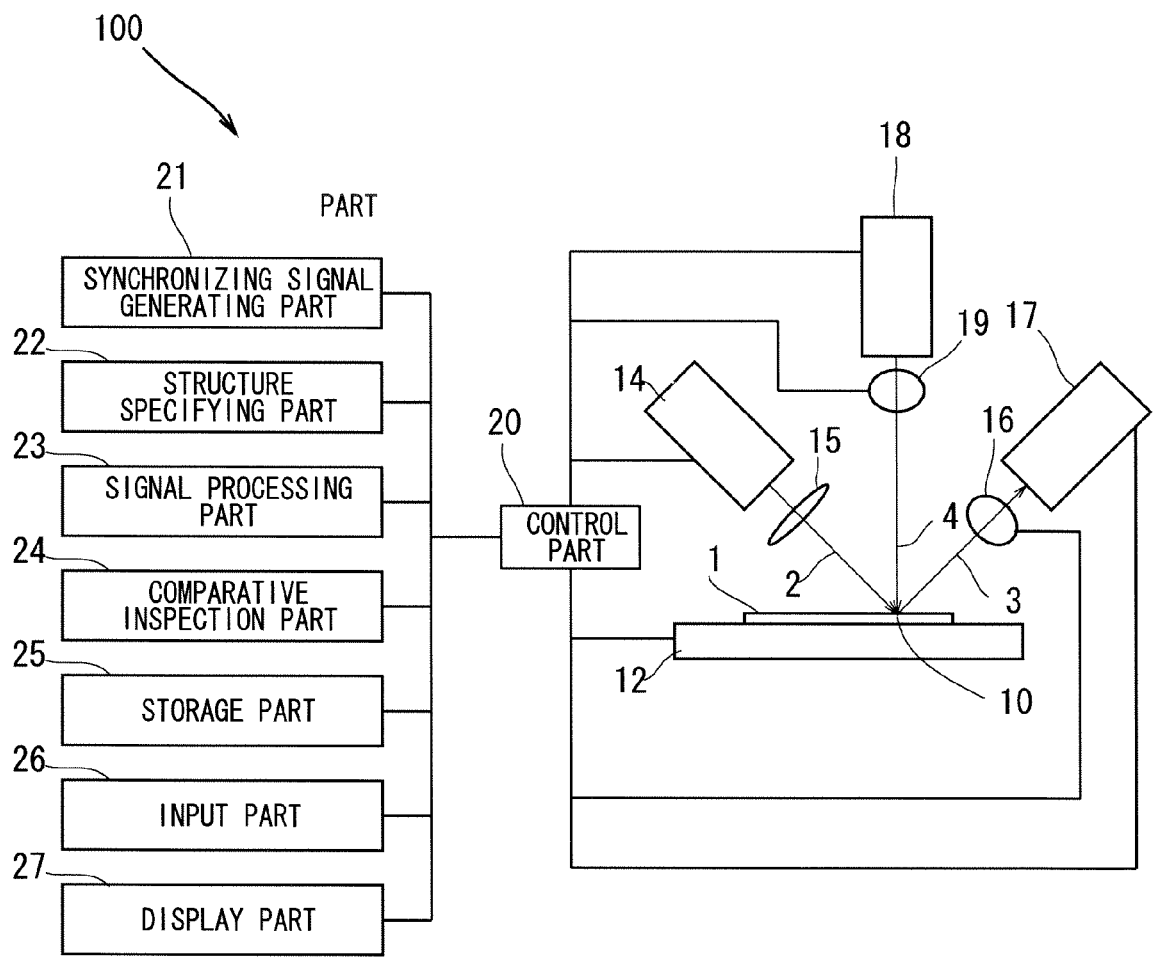
FIG. 1 schematically shows the configuration of a semiconductor inspection apparatus according to a first preferred embodiment of the present invention.

FIG. 1 schematically shows the configuration of a semiconductor inspection apparatus 100 according to a preferred embodiment of the present invention. The semiconductor inspection apparatus 100 includes a device scanning table 12, a pulsed laser light source 14, a condenser lens 15, a polarization element 16, a detection part 17, an electromagnetic wave pulse irradiation part 18, a polarization element 19, and a controller 20.

The semiconductor inspection apparatus 100 applies pulsed laser light 2 emitted from the pulsed laser light source 14 to a semiconductor device formed on a substrate 1 held on the device scanning table 12. The semiconductor inspection apparatus 100 is configured to detect the electric field strength of an electromagnetic wave pulse emitted from the substrate 1 in response to the irradiation of the pulsed laser light 2 by means of the detection part 17.

A diffusion current resulting from electrons and holes diffused and combined together is generated, for example, near a pn junction in the semiconductor device formed on the substrate 1, whereby a depletion layer containing a small number of electrons and a small number of holes is formed near the pn junction. In this region, forces which bring electrons and holes back to an n-type region and a p-type region, respectively, are generated to cause an electric field (an internal electric field). When light having energy exceeding the band gap is applied to the pn junction, photoelectrons are moved toward an n-type semiconductor by the internal electric field, and holes left behind are moved toward a p-type semiconductor. That is, the irradiation of the pulsed laser light to a region where photo-excited carriers are generated (e.g., a depletion layer) causes the photo-excited carriers to be accelerated and moved by the internal electric field. This results in the generation of a current in the form of pulses.

When a change occurs in current over time, an electromagnetic wave is generated in accordance with Maxwell equations. This electromagnetic wave is emitted in accordance with characteristics of the region where photo-excited carriers are generated such as the depletion layer. Thus, an analysis of the detected electromagnetic wave allows an inspection of the characteristics of the region where photo-excited carriers are generated. Based on this principle, the semiconductor inspection apparatus 100 is configured to detect the electromagnetic wave pulse emitted in response to the irradiation of pulsed laser light having a predetermined wavelength to the substrate 1.

More photo-excited carriers are moved, when a reverse bias is applied to the region where photo-excited carriers are generated by the application of an external voltage. This provides a relatively higher electric field strength of the generated electromagnetic wave pulse. The semiconductor inspection apparatus 100 according to the present preferred embodiment applies a reverse bias in a non-contacting manner by the irradiation of a high-intensity electromagnetic wave pulse (a reverses-biasing electromagnetic wave pulse 4), which will be described later in detail.

The device scanning table 12 holds the substrate 1, and moves the substrate 1 in a two-dimensional plane. This allows the irradiation of the pulsed laser light 2 to various locations of the substrate 1. An exemplary movement mechanism for the device scanning table 12 may include an X-Y table driven by a driving source such as a linear motor. The device scanning table 12 moves the substrate 1 in a two-dimensional plane to move an irradiation position 10 of the pulsed laser light 2 relative to the substrate 1, thereby achieving two-dimensional scanning. In the present preferred embodiment, the device scanning table 12 constitutes a scanning mechanism.

Also, the irradiation position 10 of the pulsed laser light 2 on the substrate 1 may be made changeable by controlling the pulsed laser light source 14 and the like. Although not shown, the device scanning table 12 is movable also in a direction (in this case, a vertical direction) perpendicular to the aforementioned two-dimensional plane. Moving the substrate 1 in a vertical direction allows an adjustment to be made to a distance between the substrate 1 and the pulsed laser light source 14 or between the substrate 1 and the electromagnetic wave pulse irradiation part 18.

The pulsed laser light source 14 generates the pulsed laser light 2. The condenser lens 15 concentrates the pulsed laser light 2 generated by the pulsed laser light source 14 on the substrate 1. In the present preferred embodiment, the pulsed laser light source 14 and the condenser lens 15 constitute a first irradiation part. It is preferable that the pulsed laser light 2 is applied to the back surface (the opposite surface from the surface on which the semiconductor device is formed) of the substrate 1 so as to prevent damages to the substrate 1 and to ensure the irradiation to a location in which a built-in electric field is generated, such as a pn junction and a metal-semiconductor interface.

The pulsed laser light source 14 generates the pulsed laser light 2 having a wavelength, for example, in the range of 0.3 to 2 μm (more preferably, 0.3 to 1.6 μm). The wavelength of the pulsed laser light 2 is preferably selected in accordance with the band gap of the substrate 1, for example. As an example, when the substrate 1 is mainly made of Si (silicon), it is preferable that the pulsed laser light 2 is in the range of near-infrared (e.g. not more than 1.5 μm in wavelength) to visible regions. When the substrate 1 is mainly made of a wide-gap semiconductor such as SiC (silicon carbide), it is preferable that the pulsed laser light 2 is ultraviolet light (not more than 450 μm in wavelength).

It is also preferable that the pulsed laser light 2 has time-averaged energy in the range of 0.1 mW to 10 W and a pulse width in the range of 1 femtosecond to 10 picoseconds, as disclosed in Japanese Patent Application Laid-Open No. 2006-24774. The use of the pulsed laser light 2 having such a small pulse width allows the excitation of an electromagnetic wave pulse 3 without damages to the semiconductor device (or an integrated circuit) formed on the substrate 1.

There is a danger that the substrate 1 is damaged because of the pulsed laser light 2 having too high a laser intensity, when the pulsed laser light 2 has a wavelength greater than 2 μm, time-averaged energy greater than 10 W, or a pulse width greater than 10 picoseconds. It is therefore desired that the wavelength, time-averaged energy and pulse width of the pulsed laser light 2 are set to meet the aforementioned conditions.

The polarization element 16 is an element for detecting the polarization direction of the electromagnetic wave pulse 3 entering the detection part 17. The detection part 17 detects the electric field strength of the electromagnetic wave pulse 3 emitted in response to the irradiation of the pulsed laser light 2, based on the position (irradiation position) to which the pulsed laser light 2 is applied on the substrate 1. Thus, the detection part 17 detects the electromagnetic wave pulse 3 by means of a detector including a nonlinear optical crystal, a photoconductive switch, and the like.

More specifically, part of the pulsed laser light 2 emitted from the pulsed laser light source 14 is applied in the form of probe light to the detector provided in the detection part 17. A signal responsive to the electric field strength of the electromagnetic wave pulse 3 reaching the detector at the instant when the probe light is applied to the detector is outputted from the detector. The waveform of the electromagnetic wave pulse 3 over time is restored by making the time at which the probe light reaches the detector earlier or later relative to the time at which the electromagnetic wave pulse 3 reaches the detector. A Fourier transform may be performed on the restored waveform of the electromagnetic wave pulse 3 over time to acquire the spectrum of the electromagnetic wave pulse 3 (terahertz time-domain spectroscopy). Change in the time at which the probe light reaches the detector may be achieved, for example, by changing the optical path length (optical distance) of the probe light.

When the frequency of the electromagnetic wave pulse 3 to be detected is not greater than 1 THz (terahertz), a Schottky diode may be used as the detector.

The electromagnetic wave pulse irradiation part 18 generates the reverses-biasing electromagnetic wave pulse 4. The reverses-biasing electromagnetic wave pulse 4 emitted from the electromagnetic wave pulse irradiation part 18 passes though the polarization element 19 provided at some midpoint in the path of the reverses-biasing electromagnetic wave pulse 4, so that the polarization direction thereof is adjusted to a single direction. The reverses-biasing electromagnetic wave pulse 4 which is adjusted in polarization direction is irradiated to the irradiation position 10 which receives the pulsed laser light 2 on the substrate 1. The application of the reverses-biasing electromagnetic wave pulse 4 allows the application of an electric field to the irradiation position 10. In the present preferred embodiment, the electromagnetic wave pulse irradiation part 18 and the polarization element 19 constitute a second irradiation part.

A technique for generating a high-intensity terahertz wave (a terahertz wave having a frequency in the range of 0.01 to 10 THz) has been reported (See "New Terahertz Industry" edited by Masayoshi Tonouchi, CMC Publishing Co., Ltd. (2011) p. 226). Specifically, a terahertz wave pulse having a peak electric field value in the range of 100 kV/cm to 1 MV/cm is available. This electric field value is much greater than the internal electric field (in the range of 1 to 10 kV/cm) of a transistor, and is a high-intensity electric field value (300 to 600 kV/cm) which is great enough to cause an electrical breakdown of a semiconductor. The present preferred embodiment uses this technique to emit a high-intensity terahertz wave pulse as the reverses-biasing electromagnetic wave pulse 4 from the electromagnetic wave pulse irradiation part 18. Specifically, the present preferred embodiment is designed to irradiate pulsed laser light emitted from a pulsed laser light source (femtosecond laser) to a nonlinear optical crystal to generate the reverses-biasing electromagnetic wave pulse 4 in a terahertz region from the nonlinear optical crystal.

In the semiconductor inspection apparatus 100, the optical axis (the central axis of a light beam) of the pulsed laser light 2 and the optical axis of the reverses-biasing electromagnetic wave pulse 4 are set so as not to coincide with each other. Specifically, the pulsed laser light 2 in the present preferred embodiment is directed at an incident angle of 45 degrees with respect to a main surface (front surface) of the substrate 1 placed on the device scanning table 12. The reverses-biasing electromagnetic wave pulse 4, on the other hand, is directed at an incident angle of 90 degrees with respect to (i.e., perpendicularly to) the main surface of the substrate 1. Further, the detection part 17 in the present preferred embodiment is disposed so as to detect the electromagnetic wave pulse 3 directed at a reflection angle of 45 degrees with respect to the main surface of the substrate 1. It should be noted that the incident angles at which the pulsed laser light 2 and the reverses-biasing electromagnetic wave pulse 4 are directed, and the reflection angle at which the electromagnetic wave pulse 3 is detected are not limited to the aforementioned values, but may be varied as appropriate.

The controller 20 includes components similar to those of a typical computer, such as a CPU and a RAM, which are not shown. The controller 20 is connected to the device scanning table 12, the pulsed laser light source 14, the polarization element 16, the detection part 17, the electromagnetic wave pulse irradiation part 18 and the polarization element 19 to control the operations of these components and to receive various signals outputted from these components. The controller 20 is also connected to a synchronizing signal generating part 21, a structure specifying part 22, a signal processing part 23, a comparative inspection part 24, a storage part 25, an input part 26 and a display part 27.

The synchronizing signal generating part 21, the structure specifying part 22, the signal processing part 23 and the comparative inspection part 24 may be formed by a specialized circuit. However, at least one or all of the parts 21, 22, 23 and 24 may be implemented as a functional component by the CPU of the controller 20 executing a program (inspection software) developed in the RAM. Such a program is stored in a call ready state, for example, in the storage part 25 (or in a ROM not shown).

The synchronizing signal generating part 21 generates a timing signal for causing the components of the semiconductor inspection apparatus 100 to operate in synchronism with each other. The timing signal is sent to the controller 20, and is used for controlling the components in synchronism with each other.

The structure specifying part 22 specifies the structure of a semiconductor in a location to be inspected on the substrate 1 (i.e., the irradiation position 10 which receives the pulsed laser light 2) from CAD data or information given from infrared light. In the present preferred embodiment, the direction of the electric field applied to the irradiation position 10 is determined by the reverses-biasing electromagnetic wave pulse 4, based on the structure specified by the structure specifying part 22, which will be described later in detail.

The signal processing part 23 processes a detection signal detected by the detection part 17. Specifically, the signal processing part 23 acquires the electric field strength of the electromagnetic wave pulse 3 from the detection signal of the detection part 17, restores the waveform of the electromagnetic wave pulse 3 over time, and performs a Fourier transform on the restored waveform over time to acquire a frequency fingerprint spectrum.

The comparative inspection part 24 makes a comparison between data (inspection data) acquired by the signal processing part 23 and previously prepared non-defective product data. The comparative inspection part 24 judges the inspected substrate 1 as a defective product when the result of the comparison between the inspection data and the non-defective product data exceeds a judging threshold value. The judging threshold value may be previously determined as a defined value or be set based on user's input operation. The judgment of the comparative inspection part 24 may be made for each die of the substrate 1 or for each LSI circuit.

The storage part 25 is formed by the storage of a hard disk for storing data. The storage part 25 may be formed by other portable storage media (e.g., an optical medium such as a CD and a DVD, a magnetic medium such as an MO, and a USB memory). The controller 20 and the storage part 25 may be connected via a network not shown.

The input part 26 may be formed by various input devices such as a keyboard and a mouse. A user of the semiconductor inspection apparatus 100 is allowed to perform various input operations (e.g., to input various set values) via the input part 26. The display part 27 is formed by a liquid crystal display and the like. The display part 27 may be formed by a touch panel so as to function also as the input part 26.

Figure 2:
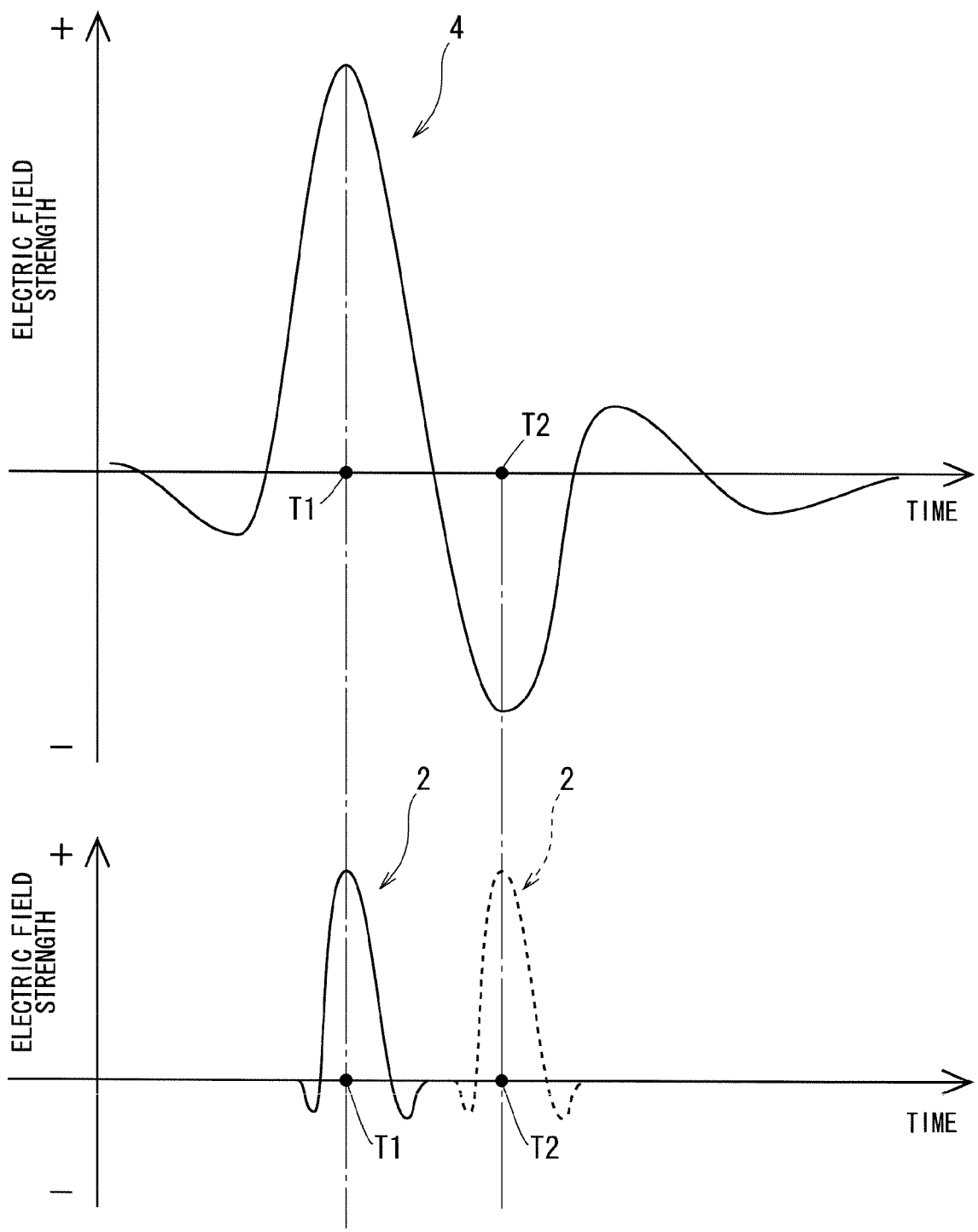
FIG. 2 is a graph showing waveforms of a reverse-biasing electromagnetic wave pulse (in an upper part) and pulsed laser light (in a lower part) over time.

FIG. 2 is a graph showing waveforms of the reverses-biasing electromagnetic wave pulse 4 (in an upper part) and the pulsed laser light 2 (in a lower part) over time. In FIG. 2, the abscissa represents time and the ordinate represents the electric field strength.

As shown in FIG. 2, the reverses-biasing electromagnetic wave pulse 4 has a waveform such that the electric field strength changes in a positive direction and in a negative direction over time. The reference character T1 denotes the time at which the electric field strength is maximized in the positive direction, and the reference character T2 denotes the time at which the electric field strength is maximized in the negative direction. Causing the reverses-biasing electromagnetic wave pulse 4 to reach the irradiation position 10 at the time T1 or at the time T2 allows the application of an electric field of the highest intensity that the reverses-biasing electromagnetic wave pulse 4 can apply to the irradiation position 10. At the time T1 and the time T2, electric fields opposite in direction from each other are applied.

Appropriate setting of the direction of an electric field to be applied to the irradiation position 10 allows a reverse bias to be applied to the irradiation position 10 when the electric field is applied by the reverses-biasing electromagnetic wave pulse 4. In this case, the electric field strength of the electromagnetic wave pulse 3 generated in response to the irradiation of the pulsed laser light 2 is increased.

In the present preferred embodiment, the irradiation of the pulsed laser light 2 is synchronized with the instant at which the reverses-biasing electromagnetic wave pulse 4 in a condition as obtained at the time T1 or at the time T2 is applied to a given irradiation position 10 (i.e., the instant at which the reverse bias of the highest intensity is applied), as shown in FIG. 2. In this manner, the irradiation of the pulsed laser light 2 and the irradiation of the reverses-biasing electromagnetic wave pulse 4 is synchronized with each other. This achieves the emission of the electromagnetic wave pulse 3, with the reverse bias of the highest possible intensity applied by the application of the reverses-biasing electromagnetic wave pulse 4.

For the irradiation of the reverse bias to a portion which receives the reverses-biasing electromagnetic wave pulse 4, it is necessary to control the direction of an electric field to be applied in accordance with the type of a semiconductor (p type or n type). This will be described with reference to FIGS. 3 and 4.

Figure 3:
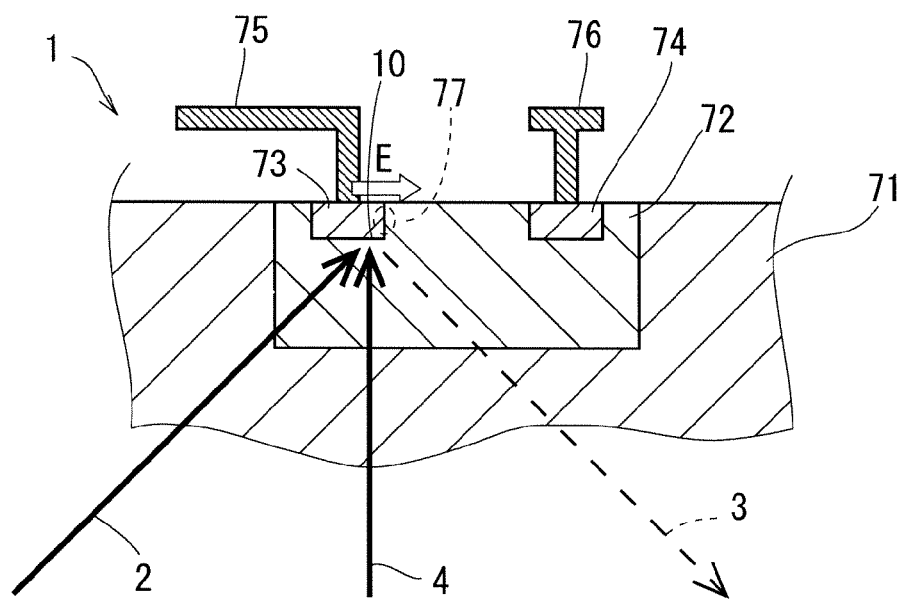
FIG. 3 is a view for illustrating the movement of photo-excited carriers upon application of a forward bias to an irradiation position.
Figure 3:
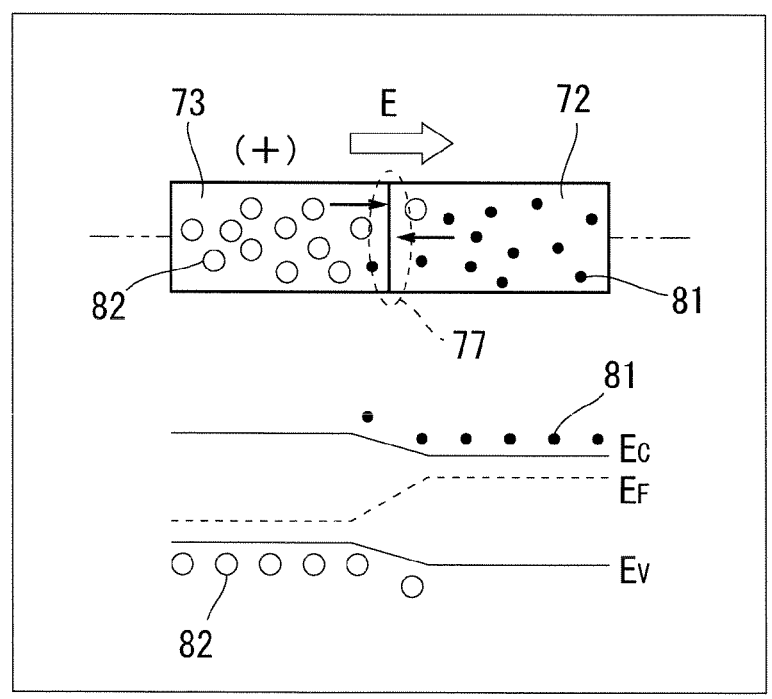
Figure 4:
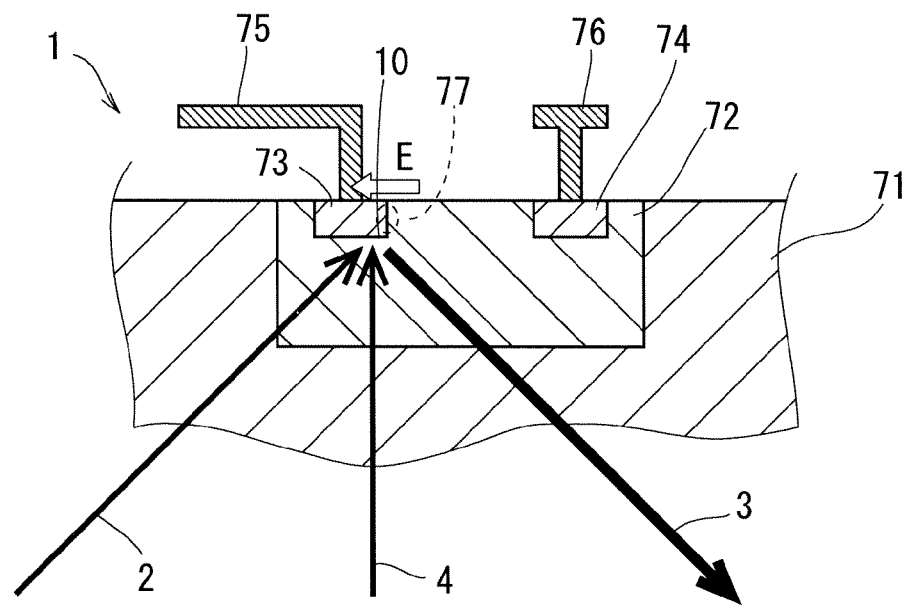
FIG. 4 is a view for illustrating the movement of photo-excited carriers upon application of a reverse bias to the irradiation position.
Figure 4:
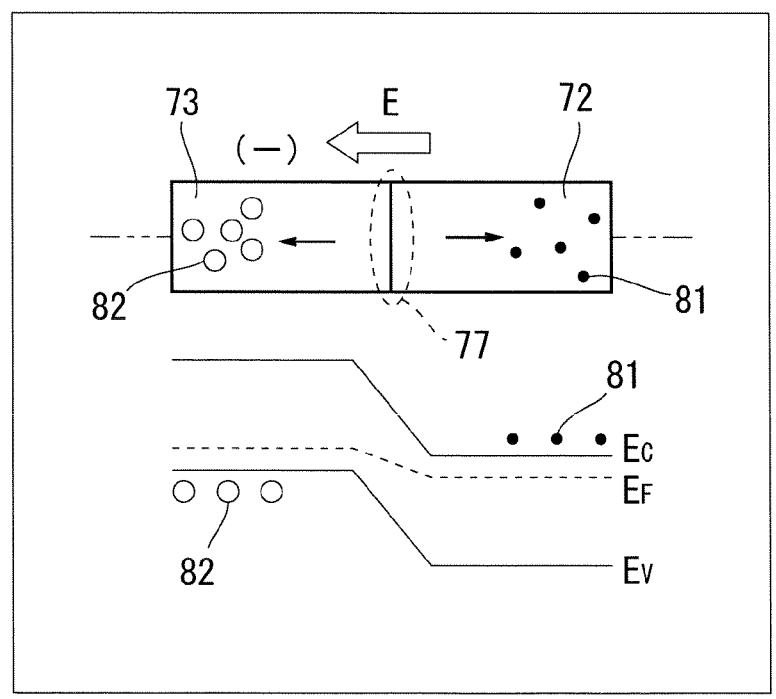

FIG. 3 is a view for illustrating the movement of photo-excited carriers upon application of a forward bias to the irradiation position 10. FIG. 4 is a view for illustrating the movement of photo-excited carriers upon application of a reverse bias to the irradiation position 10. With reference to FIGS. 3 and 4, the substrate 1 shown in sectional view has a structure such that an n-type diffusion region 72 is formed in a surface of a Si substrate 71 which is a p-type semiconductor, and such that p-type diffusion regions 73 and 74 are formed in a surface of the n-type diffusion region 72. Electrodes 75 and 76 are mounted to the p-type diffusion regions 73 and 74, respectively.

In FIGS. 3 and 4, the irradiation position 10 is defined in the p-type diffusion region 73, and the electromagnetic wave pulse 3 is shown as generated from the irradiation position 10. Also in FIGS. 3 and 4, the energy level at a pn junction 77 which is a junction between the p-type diffusion region 73 and the n-type diffusion region 72 is shown in a lower part.

With reference to FIG. 3, the reverses-biasing electromagnetic wave pulse 4 as obtained at the time T1 (i.e., at the time that the electric field strength is maximized in the positive direction) is applied to the irradiation position 10. In this case, a positive voltage is applied to the irradiation position 10 (to the p-type diffusion region 73). In other words, an external electric field E in a p-to-n direction from the p-type diffusion region 73 toward the n-type diffusion region 72 is applied. In this case, as shown in the energy level diagram, holes 82 in the p-type diffusion region 73 and electrons 81 in the n-type diffusion region 72 are readily recombined with each other at the pn junction 77, and there arises a small potential difference between the p-type diffusion region 73 and the n-type diffusion region 72 (a forward bias). Thus, if the pulsed laser light 2 is applied to the irradiation position 10 at this instant, the generated electromagnetic wave pulse 3 is relatively low in intensity.

With reference to FIG. 4, on the other hand, the reverses-biasing electromagnetic wave pulse 4 as obtained at the time T2 (i.e., at the time that the electric field strength is maximized in the negative direction) is applied to the irradiation position 10. In this case, an external negative voltage is applied to the irradiation position 10 (to the p-type diffusion region 73). In other words, an external electric field E in a n-to-p direction from the n-type diffusion region 72 toward the p-type diffusion region 73 is applied. In this case, as shown in the energy level diagram, there arises a relatively large potential difference between the p-type diffusion region 73 and the n-type diffusion region 72 (a reverse bias). That is, a state such that a positive voltage (a reverse-bias voltage) is applied to the electrode 75 is achieved in a non-contacting manner by the irradiation of the reverses-biasing electromagnetic wave pulse 4. When the pulsed laser light 2 is applied to the irradiation position 10 in this state, the generated electromagnetic wave pulse 3 is high in intensity, as compared with that obtained when the reverses-biasing electromagnetic wave pulse 4 is not applied to the irradiation position 10.

As described above, the direction of the electric field to be applied to the irradiation position 10 for the purpose of applying a reverse bias differs depending on the structure of a semiconductor in the irradiation position 10. Specifically, the irradiation of the reverse bias is accomplished by the application of the negative voltage when the portion to which the reverses-biasing electromagnetic wave pulse 4 is irradiated is a p-type semiconductor, and is accomplished by the application of the positive voltage when the aforementioned portion is not a p-type semiconductor (but is an n-type semiconductor). The direction of the electric field to be applied to the irradiation position 10 by the reverses-biasing electromagnetic wave pulse 4 is adjusted by changing the time at which the reverses-biasing electromagnetic wave pulse 4 reaches the irradiation position 10.

To adjust the time at which the reverses-biasing electromagnetic wave pulse 4 reaches the irradiation position 10, the electromagnetic wave pulse irradiation part 18 includes an optical path length change part (not shown) for changing the optical path length of the reverses-biasing electromagnetic wave pulse 4. The optical path length change part changes the optical path length from an electromagnetic wave pulse generator such as a nonlinear crystal or a photoconductive switch to the irradiation position 10 of the substrate 1. The optical path length change part changes the optical path length of the reverses-biasing electromagnetic wave pulse 4 to thereby change the time at which the reverses-biasing electromagnetic wave pulse 4 reaches the irradiation position 10. Alternatively, the time at which the reverses-biasing electromagnetic wave pulse 4 is emitted from the electromagnetic wave pulse irradiation part 18 may be changed by changing the optical path length of the pulsed laser light from the pulsed laser light source to the electromagnetic wave pulse generator. Also in this case, the time at which the reverses-biasing electromagnetic wave pulse 4 reaches the irradiation position 10 is changed.

It is difficult to directly measure the electric field strength at the time that the reverses-biasing electromagnetic wave pulse 4 reaches the irradiation position 10. Thus, the determination of the optical path length corresponding to the time T1 and the time T2 is achieved by acquiring the electric field strength of the electromagnetic wave pulse 3 generated at the time of the irradiation of the pulsed laser light 2 to the irradiation position 10 while changing the optical path length of the reverses-biasing electromagnetic wave pulse 4. Specifically, when a p-type semiconductor is set at the irradiation position 10, the time at which the electric field strength of the electromagnetic wave pulse 3 is maximized is equivalent to the time at which the reverse bias of the highest intensity is applied. The application of a reverse bias to the p-type semiconductor requires the application of a negative voltage thereto. In other words, the optical path length at this time corresponds to the time T2. The optical path length corresponding to the time T1 is acquired by setting the application position 10 at an n-type semiconductor and measuring the electromagnetic wave pulse 3 while changing the optical path length of the reverses-biasing electromagnetic wave pulse 4.

The time at which the pulsed laser light 2 reaches the irradiation position 10 may be changed while the time at which the reverses-biasing electromagnetic wave pulse 4 reaches the irradiation position 10 is fixed (i.e., while the optical path length of the reverses-biasing electromagnetic wave pulse 4 is fixed). In this case, the time at which the pulsed laser light 2 reaches the irradiation position 10 is adjusted to coincide with the time at which the strength of the electric field applied to a portion lying in the irradiation position 10 by the reverses-biasing electromagnetic wave pulse 4 is maximized. The time at which the pulsed laser light 2 reaches the irradiation position 10 is adjusted by changing the optical path length of the pulsed laser light 2.

In the present preferred embodiment, the pulsed laser light 2 is applied to the irradiation position 10 at the instant when the reverses-biasing electromagnetic wave pulse 4 of the highest electric field strength (in a condition as obtained at the time T1 or the time T2) reaches the irradiation position 10. However, it is not always necessary that the reverses-biasing electromagnetic wave pulse 4 of the highest electric field strength is irradiated to the irradiation position 10 when the pulsed laser light 2 is irradiated to the irradiation position 10. That is, the pulsed laser light 2 may be irradiated to the irradiation position 10 at the instant when the reverses-biasing electromagnetic wave pulse 4 of an electric field strength equal to or greater than a predetermined value is applied to the irradiation position 10.

When the pulsed laser light source 14 is formed by a femtosecond laser, the pulsed laser light source 14 may be used as a light source of the electromagnetic wave pulse irradiation part 18. In this case, pulsed laser light emitted from the pulsed laser light source 14 may be divided into two beams by a beam splitter and the like, so that one of the beams enters the substrate 1 and the other beam enters the electromagnetic wave pulse irradiation part 18. Such commonality of light sources allows the pulsed laser light 2 and the reverses-biasing electromagnetic wave pulse 4 to be applied to the irradiation position 10 of the substrate 1 in synchronism with each other easily. This also reduces the number of components of the semiconductor inspection apparatus 100 to reduce apparatus costs.

Next, a procedure for the inspection of the substrate 1 in the semiconductor inspection apparatus 100 will be described.

FIG. 5 is a flow diagram for the inspection of a semiconductor device in the semiconductor inspection apparatus 100. After the start of the inspection of the semiconductor device, the substrate 1 is placed on the device scanning table 12 of the semiconductor inspection apparatus 100 (in Step S1).

After the substrate 1 is placed on the device scanning table 12, the semiconductor inspection apparatus 100 sets the irradiation position 10 (in Step S2). In the present preferred embodiment, the substrate 1 of a planar shape is moved in a two-dimensional plane by the device scanning table 12. Thus, the semiconductor inspection apparatus 100 moves the substrate 1 so that the application position 10 to which the pulsed laser light 2 is irradiated coincides with an irradiation start position.

After setting the irradiation position 10, the semiconductor inspection apparatus 100 irradiates the pulsed laser light 2 toward the application position 10, and also irradiates the reverses-biasing electromagnetic wave pulse 4 toward the irradiation position 10. Then, the semiconductor inspection apparatus 100 detects the electromagnetic wave pulse 3 emitted from the substrate 1 in response to the irradiation of the pulsed laser light 2 by means of the detection part 17 (in Step S3). The details of Step S3 will be described later in detail.

During the detection of the electromagnetic wave pulse 3 in Step S3, data for restoring the waveform of the electromagnetic wave pulse 3 over time may be collected. As mentioned above, the electric field strength data for restoring the waveform of the electromagnetic wave pulse 3 over time is collected by making the time at which the probe light reaches the detector of the detection part 17 later relative to the time at which the electromagnetic wave pulse 3 reaches the detector. The electric field strength of the electromagnetic wave pulse 3 may be detected while the time at which the probe light reaches the detector is fixed relative to the electromagnetic wave pulse 3. In this case, the waveform of the electromagnetic wave pulse 3 over time cannot be restored. However, the inspection is performed rapidly because the electric field strength of the electromagnetic wave pulse 3 is sampled only at the limited time.

After the detection of the electromagnetic wave pulse 3 is completed in the irradiation position 10 set in Step S2, the semiconductor inspection apparatus 100 judges whether to change the irradiation position 10 or not (in Step S4). When it is necessary to change the irradiation position 10 for inspection, the semiconductor inspection apparatus 100 returns to Step S2. Then, the semiconductor inspection apparatus 100 moves the substrate 1 to thereby change the irradiation position 10. When there is no other place to inspect, the semiconductor inspection apparatus 100 proceeds to Step S5.

The semiconductor inspection apparatus 100 is capable of inspecting only a local part of the substrate 1. In such a case, the semiconductor inspection apparatus 100 applies the pulsed laser light 2 to the position of such a local part to detect the electromagnetic wave pulse 3 in Steps S2 and S3. Thereafter, the semiconductor inspection apparatus 100 skips Step S4 and proceeds to Step S5.

After the completion of the detection of the electromagnetic wave pulse 3, the semiconductor inspection apparatus 100 makes an analysis of the detection result (in Step S5). Specifically, the semiconductor inspection apparatus 100 makes a spectrum analysis for acquiring a frequency fingerprint spectrum, based on terahertz time-domain spectroscopy. When the electromagnetic wave pulse 3 is detected while the detection time is fixed (i.e. while the optical path length of the probe light is fixed) in Step S3, only the electric field strength of the electromagnetic wave pulse 3 at the instant when the probe light enters the detector is acquired. In this case, the waveform of the electromagnetic wave pulse 3 over time is not restored, so that Step S5 is skipped.

The semiconductor inspection apparatus 100 generates an image representing the detection result (in Step S6). Specifically, the semiconductor inspection apparatus 100 generates an image representing an electric field strength distribution of the electromagnetic wave pulse 3 or an image representing a spectrum intensity distribution of a specific frequency band, based on the spectrum analysis. When the detection time is fixed in Step S3, the semiconductor inspection apparatus 100 generates an image representing the distribution of the electric field strength of the detected electromagnetic wave pulse 3 and the like. The image generated in Step S6 may be caused to appear on the display part 27, as appropriate.

The semiconductor inspection apparatus 100 conducts a comparative inspection which makes a comparison between the inspection data acquired by the inspection and the previously prepared non-defective product data (in Step S7). Specifically, the comparative inspection part 24 judges whether the inspected substrate 1 is a non-defective product or not, based on a difference in electric field strength distribution of the electromagnetic wave pulse 3 or a difference in spectrum distribution.

Next, a detailed procedure of Step S3 will be described with reference to FIG. 6.

Figure 6:
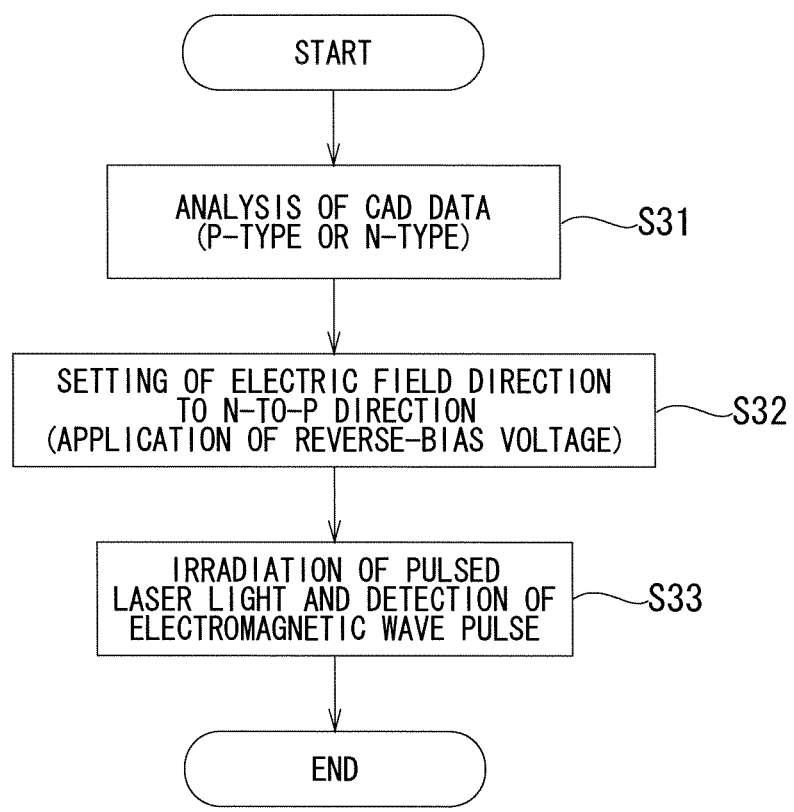
FIG. 6 is a detailed flow diagram for the detection of an electromagnetic wave pulse emitted from the application position.

FIG. 6 is a detailed flow diagram for the detection of the electromagnetic wave pulse 3 emitted from the irradiation position 10. After the start of Step S3, the structure specifying part 22 initially specifies the structure of a semiconductor in the irradiation position 10. In this case, whether the semiconductor in the irradiation position 10 is a p-type semiconductor or an n-type semiconductor is specified, based on CAD data (in Step S31). Imaging data acquired by an infrared camera or an infrared microscope may be used to establish an association between the CAD data and the actual position of the semiconductor. Infrared light, which is high in transmittance through silicon as compared with visible light, is effective in specifying the structure (e.g., shape) of a semiconductor. Thus, the irradiation position of the pulsed laser light 2 and the reverses-biasing electromagnetic wave pulse 4 is specified.

After the structure of the semiconductor is specified, the reverses-biasing electromagnetic wave pulse 4 is irradiated to the irradiation position 10 so that the direction of the electric field applied by the reverses-biasing electromagnetic wave pulse 4 is from the n-type semiconductor to the p-type semiconductor (in Step S32). The application of the electric field in the n-to-p direction in this manner allows the application of a reverse bias to the portion lying in the irradiation position 10. The pulsed laser light 2 is irradiated to the irradiation position 10 at the instant when the reverse bias is applied. The detection part 17 detects the electric field strength of the electromagnetic wave pulse 3 emitted in response to the irradiation of the pulsed laser light 2 (in Step S33).

FIG. 7 is a graph showing waveforms of the electromagnetic wave pulse 3 generated when a reverse bias is applied (a solid curve) and the electromagnetic wave pulse 3 generated when no reverse bias is applied (a broken curve) over time. As shown in FIG. 7, the application of the reverse bias increases the amplitude of the electromagnetic wave pulse 3. Thus, the sensitivity of detection by means of the detection part 17 is improved in a non-contacting manner.

The semiconductor inspection apparatus 100 is capable of irradiating the reverses-biasing electromagnetic wave pulse 4 to any location of the substrate 1. In other words, the semiconductor inspection apparatus 100 is capable of applying the reverse bias to any location. In conventional techniques, the reverse-bias voltage is applied by the connection to an external voltage application circuit, so that the place connectable to the voltage application circuit is limited. The semiconductor inspection apparatus 100, however, widens the area for inspection of the substrate 1 in a non-contacting manner because the reverse-bias voltage can be applied to various locations of the substrate 1.

The semiconductor inspection apparatus 100 is applicable to the inspection of a substrate on which a photo device as a semiconductor device is formed. The photo device is a device for converting light including visible light into current. Specific examples of the photo device include solar cells, and image sensors such as CMOS sensors and CCD sensors.

Figure 8:
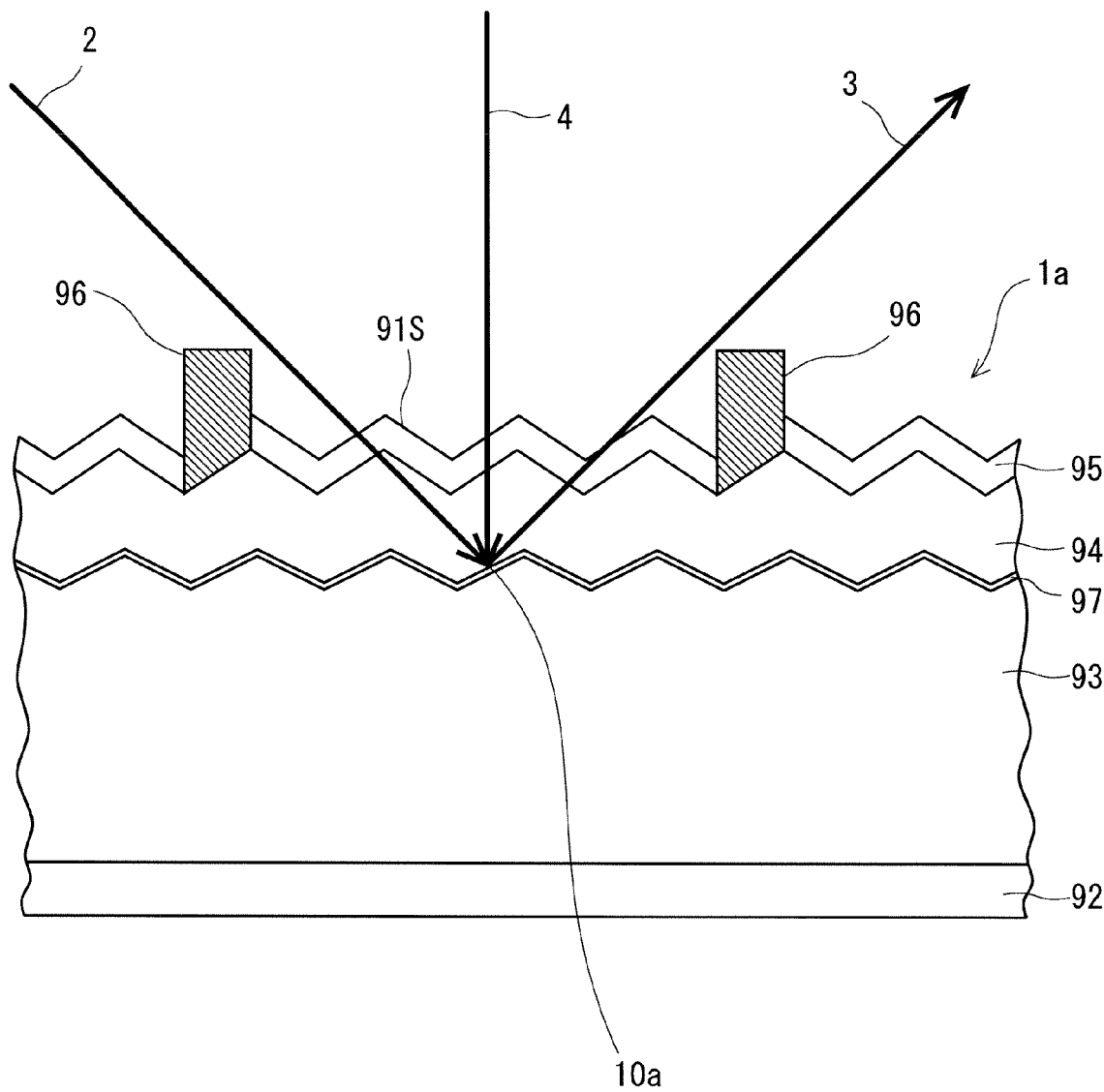
FIG. 8 is a schematic sectional view of a solar cell panel.

FIG. 8 is a schematic sectional view of a solar cell panel 1a. The solar cell panel 1a shown in FIG. 8 is formed as a thin-film crystalline silicon solar cell panel. The solar cell panel 1a is in the form of a crystalline silicon solar cell having a multi-layer structure including a planar back surface electrode 92 made of aluminum and the like, a p-type silicon layer 93, an n-type silicon layer 94, an anti-reflection film 95, and a light-receiving surface electrode 96 in a lattice form, which are arranged in bottom-to-top order. The anti-reflection film 95 is made of a material selected from the group consisting of silicon oxide, silicon nitride, and titanium oxide. One of the main surfaces of the solar cell panel 1a on which the light-receiving surface electrode 96 is provided serves as a light-receiving surface 91S. That is, the solar cell panel 1a is designed to generate electric power by receiving light on the light-receiving surface 91S. A transparent electrode may be used as the light-receiving surface electrode 96.

A junction between the p-type silicon layer 93 and the n-type silicon layer 94 is a pn junction 97 in which a depletion layer can be formed. The inspection of the pn junction 97 is conducted by setting an irradiation position 10a of the pulsed laser light 2 near the pn junction 97 and detecting the electromagnetic wave pulse 3 emitted in response to the irradiation of the pulsed laser light 2. At this time, the reverse bias is applied by applying the reverses-biasing electromagnetic wave pulse 4 in synchronism with the pulsed laser light 2 to the irradiation position 10a. Thus, the electromagnetic wave pulse 3 of high intensity is generated.

The solar cell panel 1a has a relatively simple structure such that the p-type silicon layer 93 and the n-type silicon layer 94 are vertically stacked together. It is hence easy to specify whether the portion where the irradiation position 10a is set is made of a p-type semiconductor or an n-type semiconductor. This facilitates the application of a reverse bias, as compared with the inspection of a very complicated semiconductor device such as an LSI circuit.

The light-receiving surface 91S of the solar cell panel 1a has a desired texture structure for the purpose of suppressing light reflection loss. Specifically, the light-receiving surface 91S has asperities on the order of several micrometers to tens of micrometers formed by anisotropic etching or V-shaped grooves formed by a mechanical method. In this manner, the light-receiving surface 91S of the solar cell panel 1a is in general configured to be lighted as efficiently as possible. Thus, when the pulsed laser light 2 of a predetermined wavelength is irradiated to the light-receiving surface 91S, the pulsed laser light 2 is more prone to reach the inside pn junction 97. In a solar cell panel as an example, light having a wavelength of 1 µm or less which mainly has a wavelength region of visible light is able to reach the pn junction 97 easily. In this manner, the photo device is preferable for the inspection using the irradiation of the pulsed laser light 2 in the semiconductor inspection apparatus 100.

<2. Modifications>

Although the preferred embodiment according to the present invention has been described above, the present invention is not limited to the aforementioned preferred embodiment, but various modifications may be made.

For example, the optical axis of the pulsed laser light 2 and the optical axis of the reverses-biasing electromagnetic wave pulse 4 are set so as not to coincide with each other in the aforementioned preferred embodiment. However, the pulsed laser light 2 and the reverses-biasing electromagnetic wave pulse 4 may be irradiated to the substrate 1, with the optical axes thereof coincide with each other. In this case, the electromagnetic wave pulse 3 generated from the substrate 1 may be extracted from the frequency fingerprint spectrum acquired by the signal processing part 23. Specifically, the reverses-biasing electromagnetic wave pulse 4 is adapted to have a peak intensity at 1 to 4 THz. In the case where the substrate 1 is made of Si, the analysis of components in the range of 0.1 to 0.5 THz included in the electromagnetic wave pulse 3 allows the inspection little affected by the reverses-biasing electromagnetic wave pulse 4.

The components described in the aforementioned preferred embodiment and in the various modifications may be combined together, as appropriate, unless the components are inconsistent with each other.

While the invention has been described in detail, the foregoing description is in all aspects illustrative and not restrictive. It is understood that numerous other modifications and variations can be devised without departing from the scope of the invention.

What is claimed is:

1. A semiconductor inspection apparatus for inspecting a semiconductor device, comprising:
   a first irradiation part for applying pulsed laser light to a semiconductor device;
   a second irradiation part for applying a reverse-biasing electromagnetic wave pulse for applying a reverse bias to an irradiation position which receives said pulsed laser light; and
   a detection part for detecting an electromagnetic wave pulse emitted from said irradiation position in response to the irradiation of said pulsed laser light,
   wherein said reverse-biasing electromagnetic wave pulse is a terahertz wave pulse.

2. The semiconductor inspection apparatus according to claim 1, wherein said second irradiation part uses a light source identical with a light source for generating said pulsed laser light to generate said reverse-biasing electromagnetic wave pulse.

3. The semiconductor inspection apparatus according to claim 1, wherein said second irradiation part irradiates said reverse-biasing electromagnetic wave pulse so that the direction of an electric field applied to said irradiation position by the irradiation of said reverse-biasing electromagnetic wave pulse is from an n-type semiconductor to a p-type semiconductor.

4. The semiconductor inspection apparatus according to claim 3, further comprising a structure specifying part for specifying the structure of a semiconductor in said irradiation position.

5. The semiconductor inspection apparatus according to claim 1, further comprising a scanning mechanism for moving the irradiation position of said pulsed laser light to thereby scan the semiconductor device two-dimensionally.

6. A method of inspecting a semiconductor device, comprising the steps of:
   (a) irradiating pulsed laser light having a desired wavelength to a semiconductor device;
   (b) irradiating a reverse-biasing electromagnetic wave pulse to apply a reverse bias to an irradiation position which receives said pulsed laser light in said step (a); and
   (c) detecting an electromagnetic wave pulse emitted from said irradiation position in response to the application of said pulsed laser light,
   wherein said reverse-biasing electromagnetic wave pulse is a terahertz wave pulse.

* * * * *